US007197400B2

(12) United States Patent
Liu et al.

(10) Patent No.: US 7,197,400 B2
(45) Date of Patent: Mar. 27, 2007

(54) SYSTEM AND COMPUTER SOFTWARE PRODUCTS FOR COMPARATIVE GENE EXPRESSION ANALYSIS

(75) Inventors: Wei-min Liu, Campbell, CA (US); Xiaojun Di, Sunnyvale, CA (US)

(73) Assignee: Affymetrix, Inc., Santa Clara, CA (US)

( * ) Notice: Subject to any disclaimer, the term of this patent is extended or adjusted under 35 U.S.C. 154(b) by 649 days.

(21) Appl. No.: 09/735,574

(22) Filed: Dec. 12, 2000

(65) Prior Publication Data
US 2002/0103604 A1 Aug. 1, 2002

(51) Int. Cl.
*G01N 33/48* (2006.01)
(52) U.S. Cl. ....................................... 702/19
(58) Field of Classification Search .................. 702/19, 702/22; 435/6
See application file for complete search history.

(56) References Cited

U.S. PATENT DOCUMENTS 5,800,992 A 9/1998 Fodor et al. .................... 435/6
6,040,138 A 3/2000 Lockhart et al. ............... 435/6
6,470,277 B1 * 10/2002 Chin et al. ..................... 702/19

OTHER PUBLICATIONS

Hogg, "Probability and Statistical Inference", Ch. 10, 5$^{th}$ Ed., Prentice-Hall, Inc., 1997, pp. 493-551.
Hollander, "Nonparametric Statistical Methods", Ch. 3, 2$^{nd}$ Ed., John Wiley & Sons, Inc., 1999, pp. 35-105.
Lockhart et al., Expression Monitoring by Hybridization to High Density Oligonucleotide Arrays, *Nature Biotechnology*, vol. 14, 1996, pp. 1675-1680.
Lander, "Array of Hope", *Nature-Genetics*, 1999.
Wilcoxin, "Individual Comparisons by Ranking Methods", *Biometrics*, vol. 1, 1945, pp. 80-83.

* cited by examiner

*Primary Examiner*—Michael Borin
*Assistant Examiner*—Jerry Lin
(74) *Attorney, Agent, or Firm*—Townsend and Townsend and Crew LLP

(57) ABSTRACT

Methods and computer software products are provided for analyzing gene expression data. In one embodiment, methods, systems and computer software are provided for comparative gene expression analysis using intensity dependent normalization factors.

18 Claims, 5 Drawing Sheets

SYSTEM AND COMPUTER SOFTWARE PRODUCTS FOR COMPARATIVE GENE EXPRESSION ANALYSIS

RELATED APPLICATIONS

This application is related to U.S. application Ser. No. 09/735,743, filed Dec. 12, 2000, which is incorporated herein by reference in its entirety for all purposes.

FIELD OF INVENTION

This invention is related to bioinformatics and biological data analysis. Specifically, this invention provides methods, computer software products and systems for the analysis of biological data.

BACKGROUND OF THE INVENTION

Many biological functions are carried out by regulating the expression levels of various genes, either through changes in the copy number of the genetic DNA, through changes in levels of transcription (e.g. through control of initiation, provision of RNA precursors, RNA processing, etc.) of particular genes, or through changes in protein synthesis. For example, control of the cell cycle and cell differentiation, as well as diseases, are characterized by the variations in the transcription levels of a group of genes.

Recently, massive parallel gene expression monitoring methods have been developed to monitor the expression of a large number of genes using nucleic acid array technology which was described in detail in, for example, U.S. Pat. No. 5,871,928; de Saizieu, et al., 1998, *Bacteria Transcript Imaging by Hybridization of total RNA to Oligonucleotide Arrays*, NATURE BIOTECHNOLOGY, 16:45–48; Wodicka et al., 1997, *Genome-wide Expression Monitoring in Saccharomyces cerevisiae*, NATURE BIOTECHNOLOGY 15:1359–1367; Lockhart et al., 1996, *Expression Monitoring by Hybridization to High Density Oligonucleotide Arrays*. NATURE BIOTECHNOLOGY 14:1675–1680; Lander, 1999, *Array of Hope*, NATURE-GENETICS, 21(suppl.), at 3.

Massive parallel gene expression monitoring experiments generate unprecedented amounts of information. For example, a commercially available GeneChip® array set is capable of monitoring the expression levels of approximately 6,500 murine genes and expressed sequence tags (ESTs) (Affymetrix, Inc, Santa Clara, Calif., USA). Array sets for approximately 60,000 human genes and EST clusters, 24,000 rat transcripts and EST clusters and arrays for other organisms are also available from Affymetrix. Effective analysis of the large amount of data may lead to the development of new drugs and new diagnostic tools. Therefore, there is a great demand in the art for methods for organizing, accessing and analyzing the vast amount of information collected using massive parallel gene expression monitoring methods.

SUMMARY OF THE INVENTION

Methods, systems and computer software are provided for comparing gene expression experiment results using two or more nucleic acid probe arrays.

Normalization is often, but not always, a necessary and fundamental step for comparison of results from two or more probe arrays. A normalization factor (f) is used to adjust signals from probe arrays (e.g., intensity values) to compensate for array to array variations or variations due to other factors, such as sample preparation. If $I^{(1)}$ is the intensity from a first probe array, $I^{(2)}$ from a second probe array and the normalization factor f is such that $I^{(1)}$ and $fI^{(2)}$ are comparable.

In one aspect of the invention, computer implemented methods for calculating a normalization factor are provided. The methods include providing a first intensity value ($I^{(1)}$) of a probe in a first probe array and a second intensity value ($I^{(2)}$) of the probe in a second probe array; obtaining the geometric mean ($x=\sqrt{I^{(1)}I^{(2)}}$) of $I^{(1)}$ and $I^{(2)}$; calculating said normalization factor according to: $f(x)=e^{h(x)}$, where $h(x)$ is derived from referential intensities from the first and second probe arrays. $h(x)$ may be derived by relating geometric means ($x_i$) of first referential intensities ($RI_i^{(1)}$) in the first probe array and second referential intensities ($RI_i^{(2)}$) in the second probe array to:

$$y_i = \log\left(\frac{RI_i^{(1)}}{RI_i^{(2)}}\right).$$

In some preferred embodiments, $h(x)$ is derived by sorting $(x_i, y_i)$ pairs according to $x_i$ into a plurality (m number) of bins with no overlapping; computing medians ($\bar{x}_k$) of $x_i$'s and medians ($\bar{y}_k$) of $y_i$'s for each bin; and interpolating the medians ($\bar{x}_k, \bar{y}_k$). The bins may be of approximately equal size. In some particularly preferred embodiments, $h(x)$ is:

$$h(x) = \begin{cases} \bar{y}_1, & \text{if } x \leq \bar{x}_1 \\ w\bar{y}_i + (1-w)\bar{y}_{i+1}, & \text{if } x\in(\bar{x}_i, \bar{x}_i+1], w = \frac{\bar{x}_{i+1}-x}{\bar{x}_{i+1}-\bar{x}_i}, i=1,\ldots,m-1, \\ \bar{y}_m, & \text{if } x > \bar{x}_m. \end{cases}$$

In one particularly preferred embodiment, m is 3.

Computer implemented methods for comparing the expression of a gene in a first sample with a second sample are also provided. The methods may include steps of providing a first plurality of intensity values ($I_i^{(1)}$), each of which reflects the expression of the gene in the first sample, where the intensity values are obtained from a first nucleic acid probe array; providing a second plurality of intensity values ($I_i^{(2)}$), each of which reflects the expression of the gene in the second sample, wherein the intensity values are obtained from a second nucleic acid probe array; calculating a p-value using one-sided Wilcoxon's signed rank test, wherein the p-value is for a null hypothesis that median(f(x)$I_i^{(2)}-I_i^{(1)}$)=0 and an alternative hypothesis that median(f(x)$I_i^{(1)}-I_i^{(2)}$)>0, wherein said f(x) is a normalization factor; and indicating whether the expression of gene is increased in the second sample in comparison with the first sample based upon said p-value. Each of the intensity values may be from one probe (such as a probe that is designed to target the transcript of the gene) on the nucleic acid probe arrays.

The normalization factor ($f(x)$) may be calculated by obtaining the geometric mean (x) of $I_i^{(1)}$ and $I_i^{(2)}$; calculating the normalization factor according to: $f(x)=e^{h(x)}$, where the $h(x)$ is derived from referential intensities from the first and second probe arrays. In some embodiments, $h(x)$ is derived by relating geometric means ($x_i$) of first referential intensities ($RI_i^{(1)}$) in the first probe array and the second referential intensities ($RI_i^{(2)}$) in said second probe array to:

$$y_i = \log\left(\frac{RI_i^{(1)}}{RI_i^{(2)}}\right).$$

In some preferred embodiments, h(x) is derived by sorting $(x_i, y_i)$ pairs according to $x_i$ into a plurality (m number) of bins with no overlapping; computing medians ($\bar{x}_k$) of $x_i$'s and medians ($\bar{y}_k$) of $y_i$'s for each bin; and interpolating the medians ($\bar{x}_k, \bar{y}_k$). The bins may be of equal size. In some particularly preferred embodiments, h(x) is:

$$h(x) = \begin{cases} \bar{y}_1, & \text{if } x \leq \bar{x}_1 \\ w\bar{y}_i + (1-w)\bar{y}_{i+1}, & \text{if } x \in (\bar{x}_i, \bar{x}_i+1], w = \frac{\bar{x}_{i+1} - x}{\bar{x}_{i+1} + -\bar{x}_i}, i = 1, \ldots, m-1, \\ \bar{y}_m, & \text{if } x > \bar{x}_m. \end{cases}$$

In one particularly preferred embodiment, m is 3.

In another aspect of the invention, computer software products and systems for performing the methods of the invention are also provided. The computer software product includes code for performing the steps of the method of the invention and a computer readable medium for storing the code. A system of the invention includes a processor; and a memory being coupled with the processor, the memory storing a plurality of machine instructions that cause the processor to perform the method steps of the invention.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE PREFERRED EMBODIMENTS

Figure 1:
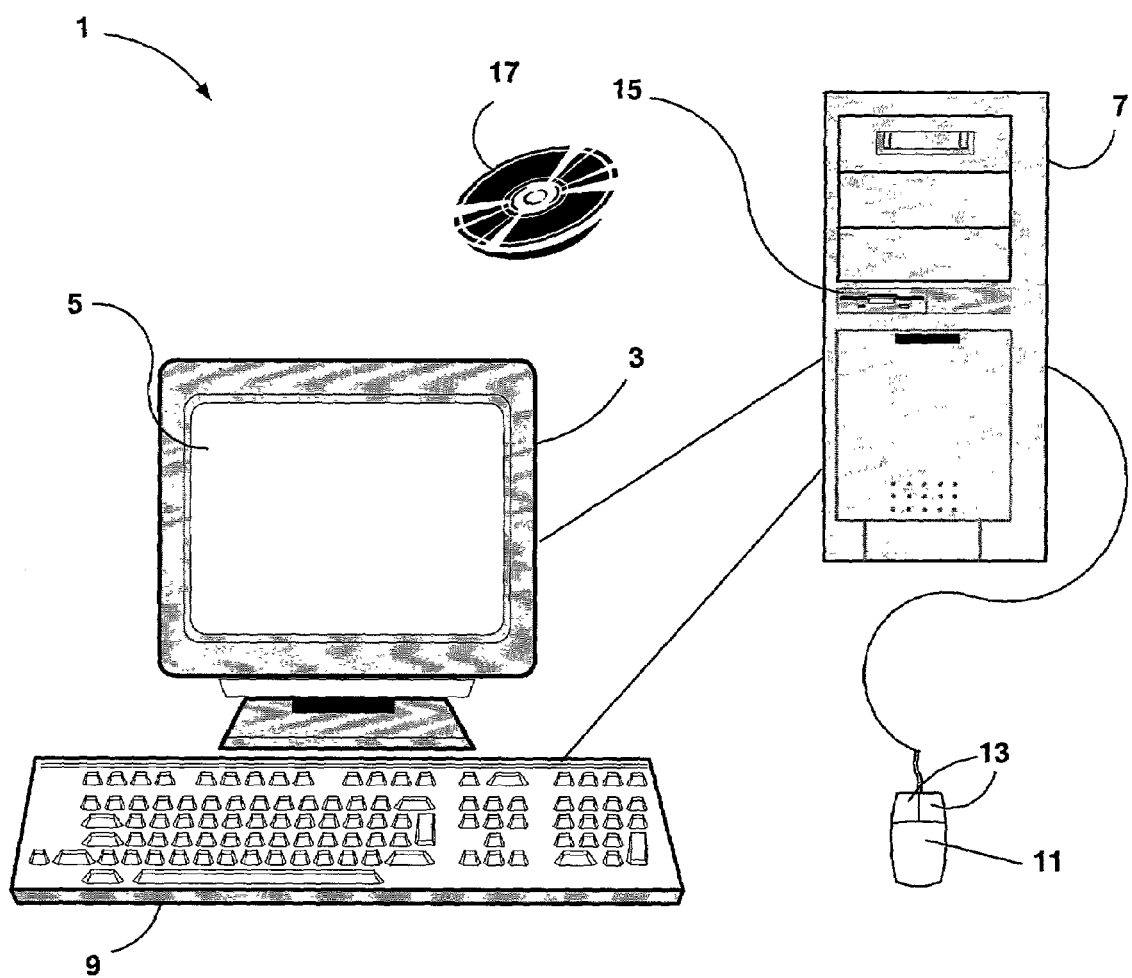
FIG. 1 illustrates an example of a computer system that may be utilized to execute the software of an embodiment of the invention.

Reference will now be made in detail to the preferred embodiments of the invention. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention. All cited references, including patent and non-patent literature, are incorporated herein by reference in their entireties for all purposes.

I. Gene Expression Monitoring with High Density Oligonucleotide Probe Arrays High density nucleic acid probe arrays, also referred to as "DNA Microarrays," have become a method of choice for monitoring the expression of a large number of genes. As used herein, "Nucleic acids" may include any polymer or oligomer of nucleosides or nucleotides (polynucleotides or oligonucleotidies), which include pyrimidine and purine bases, preferably cytosine, thymine, and uracil, and adenine and guanine, respectively. See Albert L. Lehninger, PRINCIPLES OF BIOCHEMISTRY, at 793–800 (Worth Pub. 1982) and L. Stryer BIOCHEMISTRY, 4$^{th}$ Ed., (March 1995), both incorporated by reference. "Nucleic acids" may include any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. Oligonucleotides and polynucleotides are included in this definition and relate to two or more nucleic acids in a polynucleotide.

"A target molecule" refers to a biological molecule of interest. The biological molecule of interest can be a ligand, receptor, peptide, nucleic acid (oligonucleotide or polynucleotide of RNA or DNA), or any other of the biological molecules listed in U.S. Pat. No. 5,445,934 at col. 5, line 66 to col. 7, line 51. For example, if transcripts of genes are the interest of an experiment, the target molecules would be the transcripts. Other examples include protein fragments, small molecules, etc. "Target nucleic acid" refers to a nucleic acid (often derived from a biological sample) of interest. Frequently, a target molecule is detected using one or more probes. As used herein, a "probe" is a molecule for detecting a target molecule. It can be any of the molecules in the same classes as the target referenced above. A probe may refer to a nucleic acid, such as an oligonucleotide, capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, the bases in probes may be joined by a linkage other than a phosphodiester bond, so long as the bond does not interfere with hybridization. Thus, probes may be peptide nucleic acids in which the constituent bases are joined by peptide bonds rather than phosphodiester linkages. Other examples of probes include antibodies used to detect peptides or other molecules, any ligands for detecting its binding partners. When referring to targets or probes as nucleic acids, it should be understood that these are illustrative embodiments that are not to limit the invention in any way.

In preferred embodiments, probes may be immobilized on substrates to create an array. An "array" may comprise a solid support with peptide or nucleic acid or other molecular probes attached to the support. Arrays typically comprise a plurality of different nucleic acids or peptide probes that are coupled to a surface of a substrate in different, known locations. These arrays, also described as "microarrays" or colloquially "chips" have been generally described in the art, for example, in Fodor et al., Science, 251:767–777 (1991), which is incorporated by reference for all purposes. Methods of forming high density arrays of oligonucleotides, peptides and other polymer sequences with a minimal number of synthetic steps are disclosed in, for example, U.S. Pat. Nos. 5,143,854, 5,252,743, 5,384,261, 5,405,783, 5,424,186, 5,429,807, 5,445,943, 5,510,270, 5,677,195, 5,571,639, 6,040,138, all incorporated herein by reference for all purposes. The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668, U.S. Pat. Nos. 5,677,195, 5,800,992 and 6,156,501 which disclose methods of forming vast arrays of peptides, oligonucleotides and other molecules using, for example, light-directed synthesis techniques. See also, Fodor et al., Science, 251, 767–77 (1991). These procedures for synthesis of polymer arrays are now referred to as VLSIPS™ procedures. Using the VLSIPS™ approach, one heterogeneous array of polymers is converted, through simultaneous coupling at a number of reaction sites, into a different heterogeneous array. See, U.S. Pat. Nos. 5,384,261 and 5,677,195.

Methods for making and using molecular probe arrays, particularly nucleic acid probe arrays are also disclosed in, for example, U.S. Pat. Nos. 5,143,854, 5,242,974, 5,252, 743, 5,324,633, 5,384,261, 5,405,783, 5,409,810, 5,412,087, 5,424,186, 5,429,807, 5,445,934, 5,451,683, 5,482,867, 5,489,678, 5,491,074, 5,510,270, 5,527,681, 5,527,681, 5,541,061, 5,550,215, 5,554,501, 5,556,752, 5,556,961, 5,571,639, 5,583,211, 5,593,839, 5,599,695, 5,607,832, 5,624,711, 5,677,195, 5,744,101, 5,744,305, 5,753,788, 5,770,456, 5,770,722, 5,831,070, 5,856,101, 5,885,837, 5,889,165, 5,919,523, 5,922,591, 5,925,517, 5,658,734, 6,022,963, 6,150,147, 6,147,205, 6,153,743, 6,140,044 and D430024, all of which are incorporated by reference in their entireties for all purposes.

Typically, a nucleic acid sample is a labeled with a signal moiety, such as a fluorescent label. The sample is hybridized with the array under appropriate conditions. The arrays are washed or otherwise processed to remove non-hybridized sample nucleic acids. The hybridization is then evaluated by detecting the distribution of the label on the chip. The distribution of label may be detected by scanning the arrays to determine florescence intensities distribution. Typically, the hybridization of each probe is reflected by several pixel intensities. The raw intensity data may be stored in a gray scale pixel intensity file. The GATC™ Consortium has specified several file formats for storing array intensity data. The final software specification is available at the website of the GATC™ Consortium and is incorporated herein by reference in its entirety. The pixel intensity files are usually large. For example, a GATC™ compatible image file may be approximately 50 Mb if there are about 5000 pixels on each of the horizontal and vertical axes and if a two byte integer is used for every pixel intensity. The pixels may be grouped into cells (see, GATC™ software specification). The probes in a cell are designed to have the same sequence (i.e., each cell is a probe area). A CEL file contains the statistics of a cell, e.g., the 75 percentile and standard deviation of intensities of pixels in a cell. The 75 percentile of pixel intensity of a cell is often used as the intensity of the cell. Methods for signal detection and processing of intensity data are additionally disclosed in, for example, U.S. Pat. Nos. 5,547, 839, 5,578,832, 5,631,734, 5,800,992, 5,856,092, 5,936,324, 5,981,956, 6,025,601, 6,090,555, 6,141,096, 6,141,096, and 5,902,723. Methods for array based assays, computer software for data analysis and applications are additionally disclosed in, e.g., U.S. Pat. Nos. 5,527,670, 5,527,676, 5,545,531, 5,622,829, 5,631,128, 5,639,423, 5,646,039, 5,650,268, 5,654,155, 5,674,742, 5,710,000, 5,733,729, 5,795,716, 5,814,450, 5,821,328, 5,824,477, 5,834,252, 5,834,758, 5,837,832, 5,843,655, 5,856,086, 5,856,104, 5,856,174, 5,858,659, 5,861,242, 5,869,244, 5,871,928, 5,874,219, 5,902,723, 5,925,525, 5,928,905, 5,935,793, 5,945,334, 5,959,098, 5,968,730, 5,968,740, 5,974,164, 5,981,174, 5,981,185, 5,985,651, 6,013,440, 6,013,449, 6,020,135, 6,027,880, 6,027,894, 6,033,850, 6,033,860, 6,037,124, 6,040,138, 6,040,193, 6,043,080, 6,045,996, 6,050,719, 6,066,454, 6,083,697, 6,114,116, 6,114,122, 6,121,048, 6,124,102, 6,130,046, 6,132,580, 6,132,996 and 6,136,269, all of which are incorporated by reference in their entireties for all purposes.

Nucleic acid probe array technology, use of such arrays, analysis array based experiments, associated computer software, composition for making the array and practical applications of the nucleic acid arrays are also disclosed, for example, in the following U.S. patent applications Ser. Nos.: 07/838,607, 07/883,327, 07/978,940, 08/030,138, 08/082, 937, 08/143,312, 08/327,522, 08/376,963, 08/440,742, 08/533,582, 08/643,822, 08/772,376, 09/013,596, 09/016, 564, 09/019,882, 09/020,743, 09/030,028, 09/045,547, 09/060,922, 09/063,311, 09/076,575, 09/079,324, 09/086, 285, 09/093,947, 09/097,675, 09/102,167, 09/102,986, 09/122,167, 09/122,169, 09/122,216, 09/122,304, 09/122, 434, 09/126,645, 09/127,115, 09/132,368, 09/134,758, 09/138,958, 09/146,969, 09/148,210, 09/148,813, 09/170, 847, 09/172,190, 09/174,364, 09/199,655, 09/203,677, 09/256,301, 09/285,658, 09/294,293, 09/318,775, 09/326, 137, 09/326,374, 09/341,302, 09/354,935, 09/358,664, 09/373,984, 09/377,907, 09/383,986, 09/394,230, 09/396, 196, 09/418,044, 09/418,946, 09/420,805, 09/428,350, 09/431,964, 09/445,734, 09/464,350, 09/475,209, 09/502, 048, 09/510,643, 09/513,300, 09/516,388, 09/528,414, 09/535,142, 09/544,627, 09/620,780, 09/640,962, 09/641, 081, 09/670,510, 09/685,011, and 09/693,204 and in the following Patent Cooperative Treaty (PCT) applications/publications: PCT/NL90/00081, PCT/GB91/00066, PCT/US91/08693, PCT/US91/09226, PCT/US91/09217, WO/93/10161, PCT/US92/10183, PCT/GB93/00147, PCT/US93/01152, WO/93/22680, PCT/US93/04145, PCT/US93/08015, PCT/US94/07106, PCT/US94/12305, PCT/GB95/00542, PCT/US95/07377, PCT/US95/02024, PCT/US96/05480, PCT/US96/11147, PCT/US96/14839, PCT/US96/15606, PCT/US97/01603, PCT/US97/02102, PCT/GB97/005566, PCT/US97/06535, PCT/GB97/01148, PCT/GB97/01258, PCT/US97/08319, PCT/US97/08446, PCT/US97/10365, PCT/US97/17002, PCT/US97/16738, PCT/US97/19665, PCT/US97/20313, PCT/US97/21209, PCT/US97/21782, PCT/US97/23360, PCT/US98/06414, PCT/US98/01206, PCT/GB98/00975, PCT/US98/04280, PCT/US98/04571, PCT/US98/05438, PCT/US98/05451, PCT/US98/12442, PCT/US98/12779, PCT/US98/12930, PCT/US98/13949, PCT/US98/15151, PCT/US98/15469, PCT/US98/15458, PCT/US98/15456, PCT/US98/16971, PCT/US98/16686, PCT/US99/19069, PCT/US98/18873, PCT/US98/18541, PCT/US98/19325, PCT/US98/22966, PCT/US98/26925, PCT/US98/27405 and PCT/IB99/00048, all of which are incorporated by reference in their entireties for all purposes. All the above cited patent applications and other references cited throughout this specification are incorporated herein by reference in their entireties for all purposes.

The embodiments of the invention will be described using GeneChip® high oligonucleotide density probe arrays (available from Affymetrix, Inc., Santa Clara, Calif., USA) as exemplary embodiments. One of skill in the art would appreciate that the embodiments of the invention are not limited to high density oligonucleotide probe arrays. In contrast, the embodiments of the invention are useful for analyzing any parallel large scale biological analysis, such as those using nucleic acid probe array, protein arrays, etc.

Gene expression monitoring using GeneChip® high density oligonucleotide probe arrays are described in, for example, Lockhart et al., 1996, Expression Monitoring By Hybridization to High Density Oligonucleotide Arrays, Nature Biotechnology 14:1675–1680; U.S. Pat. Nos. 6,040,138 and 5,800,992, all incorporated herein by reference in their entireties for all purposes.

In the preferred embodiment, oligonucleotide probes are synthesized directly on the surface of the array using photolithography and combinatorial chemistry as disclosed in several patents previous incorporated by reference. In such embodiments, a single square-shaped feature on an array contains one type of probe. Probes are selected to be specific against desired target. Methods for selecting probe sequences are disclosed in, for example, U.S. patent application Ser. No. 09/718,295, filed Nov. 21, 2000, Ser. No. 09/721,042, filed Nov. 21, 2000, and 60/252,617, filed Nov. 21, 2000, all incorporated herein by reference in their entireties for all purposes.

In a preferred embodiment, oligonucleotide probes in the high density array are selected to bind specifically to the nucleic acid target to which they are directed with minimal non-specific binding or cross-hybridization under the particular hybridization conditions utilized. Because the high density arrays of this invention can contain in excess of 1,000,000 different probes, it is possible to provide every probe of a characteristic length that binds to a particular nucleic acid sequence. Thus, for example, the high density array can contain every possible 20 mer sequence complementary to an IL-2 mRNA. There, however, may exist 20 mer subsequences that are not unique to the IL-2 mRNA. Probes directed to these subsequences are expected to cross hybridize with occurrences of their complementary sequence in other regions of the sample genome. Similarly, other probes simply may not hybridize effectively under the hybridization conditions (e.g., due to secondary structure, or interactions with the substrate or other probes). Thus, in a preferred embodiment, the probes that show such poor specificity or hybridization efficiency are identified and may not be included either in the high density array itself (e.g., during fabrication of the array) or in the post-hybridization data analysis.

Probes as short as 15, 20, 25 or 30 nucleotides are sufficient to hybridize to a subsequence of a gene and that, for most genes, there is a set of probes that performs well across a wide range of target nucleic acid concentrations. In a preferred embodiment, it is desirable to choose a preferred or "optimum" subset of probes for each gene before synthesizing the high density array.

In some preferred embodiments, the expression of a particular transcript may be detected by a plurality of probes, typically up to 5, 10, 15, 20, 30 or 40 probes. Each of the probes may target different sub-regions of the transcript. However, probes may overlap over targeted regions.

In some preferred embodiments, each target sub-region is detected using two probes: a perfect match (PM) probe that is designed to be completely complementary to a reference or target sequence. In some other embodiments, a PM probe may be substantially complementary to the reference sequence. A mismatch (MM) probe is a probe that is designed to be complementary to a reference sequence except for some mismatches that may significantly affect the hybridization between the probe and its target sequence. In preferred embodiments, MM probes are designed to be complementary to a reference sequence except for a homomeric base mismatch at the central (e.g., $13^{th}$ in a 25 base probe) position. Mismatch probes are normally used as controls for cross-hybridization. A probe pair is usually composed of a PM and its corresponding MM probe. The difference between PM and MM provides an intensity difference in a probe pair.

II. Data Analysis Systems

In one aspect of the invention, methods, computer software products and systems are provided for computational analysis of microarray intensity data for determining the presence or absence of genes in a given biological sample. Accordingly, the present invention may take the form of data analysis systems, methods, analysis software, etc. Software written according to the present invention is to be stored in some form of computer readable medium, such as memory, or CD-ROM, or transmitted over a network, and executed by a processor. For a description of basic computer systems and computer networks, see, e.g., Introduction to Computing Systems: From Bits and Gates to C and Beyond by Yale N. Patt, Sanjay J. Patel, 1st edition (Jan. 15, 2000) McGraw Hill Text; ISBN: 0072376902; and Introduction to Client/Server Systems: A Practical Guide for Systems Professionals by Paul E. Renaud, 2nd edition (June 1996), John Wiley & Sons; ISBN: 0471133337.

Computer software products may be written in any of various suitable programming languages, such as C, C++, C# (Microsoft®), Fortran, Perl, MatLab (MathWorks, www-.mathworks.com), SAS, SPSS and Java. The computer software product may be an independent application with data input and data display modules. Alternatively, the computer software products may be classes that may be instantiated as distributed objects. The computer software products may also be component software such as Java Beans (Sun Microsystem), Enterprise Java Beans (EJB, Sun Microsystems), Microsoft® COM/DCOM (Microsoft®), etc.

FIG. 1 illustrates an example of a computer system that may be used to execute the software of an embodiment of the invention. FIG. 1 shows a computer system 1 that includes a display 3, screen 5, cabinet 7, keyboard 9, and mouse 11. Mouse 11 may have one or more buttons 13 for interacting with a graphic user interface. Cabinet 7 houses a CD-ROM or DVD-ROM drive 15, system memory and a hard drive (see FIG. 2) which may be utilized to store and retrieve software programs incorporating computer code that implements the invention, data for use with the invention and the like. Although a CD 17 is shown as an exemplary computer readable medium, other computer readable storage media including floppy disk, tape, flash memory, system memory, and hard drive may be utilized. Additionally, a data signal embodied in a carrier wave (e.g., in a network including the Internet) may be the computer readable storage medium.

Figure 2:
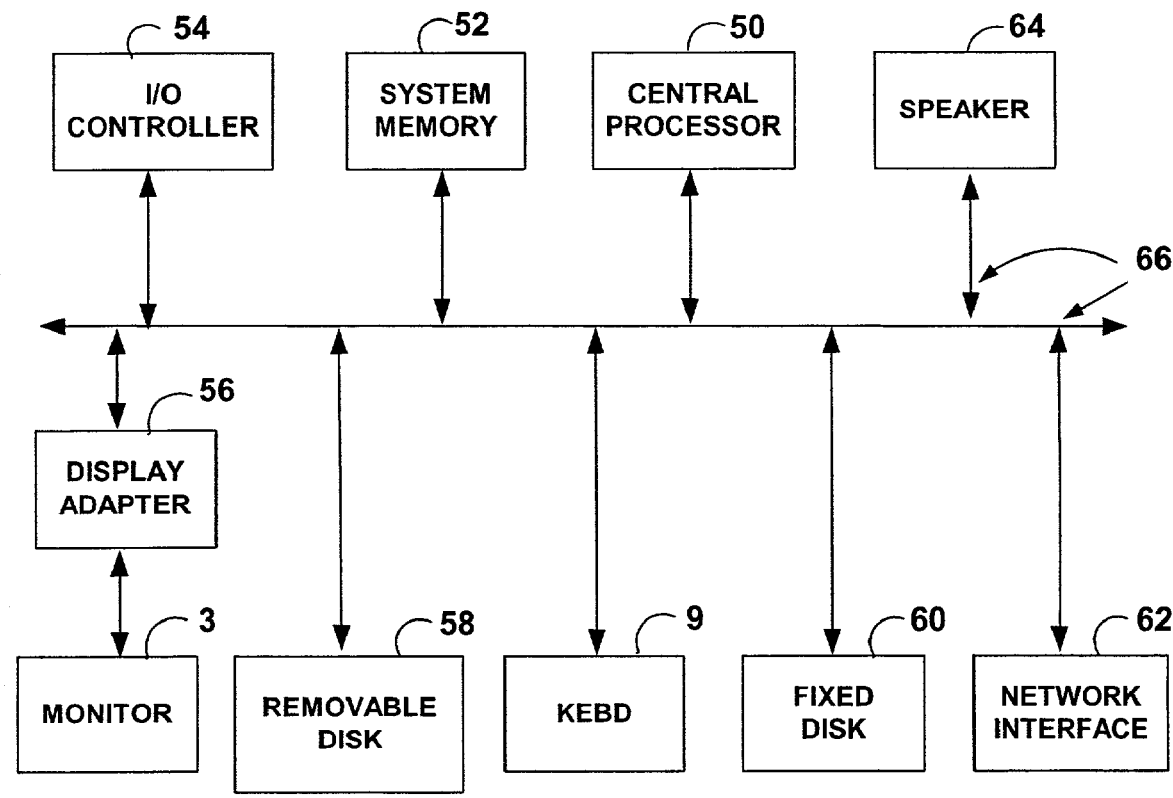
FIG. 2 illustrates a system block diagram of the computer system of FIG. 1.

FIG. 2 shows a system block diagram of computer system 1 used to execute the software of an embodiment of the invention. As in FIG. 1, computer system 1 includes monitor 3, keyboard 9, and mouse 11. Computer system 1 further includes subsystems such as a central processor 50, system memory 52, fixed storage 60 (e.g., hard drive), removable storage 58 (e.g., CD-ROM), display adapter 56, sound card, speakers 64, and network interface 62. Other computer systems suitable for use with the invention may include additional or fewer subsystems. For example, another computer system may include more than one processor 50 or a cache memory. Computer systems suitable for use with the invention may also be embedded in a measurement instrument.

III. Robust Normalization Factor

In one aspect of the invention, methods, systems and computer software are provided for comparing gene expression experiment results using two or more nucleic acid probe arrays. Frequently, nucleic acid samples derived from biological samples representing different physiological, developmental, pathological, pharmacological, or toxicological states are measured using multiple nucleic acid probe arrays. For example, a cRNA sample from cancerous cells is applied to one probe array (also referred to as a chip); and a cRNA sample from normal cells is applied to another probe array.

Normalization is often, but not always, a necessary and fundamental step for comparison of results from two or more probe arrays. A normalization factor (f) is used to adjust signals from probe arrays (e.g., intensity values) to compensate for array to array variations. Let $I^{(1)}$ be the intensity from a first probe array, $I^{(2)}$ from a second probe array and f so that $I^{(1)}$ and $fI^{(2)}$ are comparable (or $(1/f_1)I^{(1)}$ and $I^{(2)}$ are comparable). One of skill in the art would appreciate that the designation of the first probe array vs. the second probe array is for the purpose of simplifying the description of the embodiments of the invention. Any probe array may be designated as the first probe array. However, once a probe array is designated as the first probe array, the probe array that is going to be compared with the first probe array is designated as the second probe array. In preferred embodiments, the baseline probe array, i.e., the probe array that has been hybridized with a baseline nucleic acid sample, is the first probe array and the experimental probe array, i.e., the probe array that has been hybridized with an experimental nucleic acid sample, is the second probe array.

In one aspect of the invention, methods, systems and software for calculating intensity dependent normalization factor are provided. In preferred embodiments, the intensity dependent normalization factor is based upon signals from normalization control probes and/or expression level controls.

Normalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few normalization probes are used and they are selected such that they hybridize well (i.e. no secondary structure) and do not match any target-specific probes.

Expression level controls are probes that hybridize specifically with constitutively expressed genes in the biological sample. Virtually any constitutively expressed gene provides a suitable target for expression level controls. Typically expression level control probes have sequences complementary to subsequences of constitutively expressed "housekeeping genes" including, but not limited to the β-actin gene, the transferrin receptor gene, the GAPDH gene, and the like. Housekeeping genes, or maintenance genes, are those genes constitutively expressed to maintain cellular function (See, Watson, J. D., N. H. Hopkins, J. W. Roberts, J. A. Steitz, A. M. Weiner, A. M. *Molecular Biology of the Gene*, Vol. 1, 1965, which is incorporated herein in its entirety by reference for all purposes).

The number of normalization and expression level control probes may be determined according to the need of specific probe array design, sample source, experimental conditions, etc. In preferred embodiments, the probe arrays may include at least 2, 5, 10, 15, 20, 25, 50, 75, 100, 500, 1000 normalization and/or expression level control probes.

Signals from normalization probes and expression level control probes are referred to as referential intensities. Let $I_1^{(1)}, I_2^{(1)}, \ldots, I_n^{(1)}$ be the referential intensities in the first probe array, and $I_1^{(2)}, I_2^{(2)}, \ldots, I_n^{(2)}$ be the referential intensities in the second probe array. They are all positive numbers (no background subtraction is necessary in some embodiments). Let $$x_i = \sqrt{I_i^{(1)} I_i^{(2)}}, \tag{1}$$

$$y_i = \log\left(\frac{I_i^{(1)}}{I_i^{(2)}}\right) \tag{2}$$

The pairs of $(x_i, y_i)$ are sorted by $x_i$ and split them into m bins with approximately equal sizes. In some embodiments, the default values of m is 3. The $x_i$ values in one bin should have no overlap with $x_i$ values in another bin. The medians of $x_i$ and $y_i$ in each bin are calculated and let them be $(\bar{x}_k, \bar{y}k)$ (k=1, ..., m). These points of medians are interpolated. In a preferred embodiment, for a value x:

$$h(x) = \begin{cases} \overline{y}_1, & \text{if } x \le \overline{x}_1 \\ w\overline{y}_i + (1-w)\overline{y}_{i+1}, & \text{if } x\in(\overline{x}_i, \overline{x}_i+1], w = \frac{\overline{x}_{i+1} - x}{\overline{x}_{i+1} + -\overline{x}_i}, i = 1, \ldots, m-1, \\ \overline{y}_m, & \text{if } x > \overline{x}_m. \end{cases} \quad (3)$$

The normalization factor for a perfect match cell with intensity $I^{(1)}$ in the first probe array and the intensity $I^{(2)}$ in the second probe array with geometric mean $x=\sqrt{I^{(b)}I^{(e)}}$ is set to be $$f(x)=e^{h(x)}. \quad (4)$$

In some embodiments, low intensity space normalization cells are also included in the computation. Therefore, the space-dependency of normalization factor is also indirectly included in intensity-dependency.

In one aspect of the invention, computer implemented methods for calculating a normalization factor are provided. The methods include providing a first intensity value ($I^{(1)}$) of a probe in a first probe array and a second intensity value ($I^{(2)}$) of the probe in a second probe array; obtaining the geometric mean ($x=\sqrt{I^{(1)}I^{(2)}}$) of $I^{(1)}$ and $I^{(2)}$; calculating said normalization factor according to: $f(x)=e^{h(x)}$, where $h(x)$ is derived from referential intensities from the first and second probe arrays. $h(x)$ may be derived by relating geometric means ($x_i'$) of first referential intensities ($RI_i^{(1)}$) in the first probe array and second referential intensities ($RI_i^{(2)}$) in the second probe array to:

$$y_i = \log\left(\frac{RI_i^{(1)}}{RI_i^{(2)}}\right).$$

In some preferred embodiments, $h(x)$ is derived by sorting ($x_i'$, $y_i'$) pairs according to $x_i'$ into a plurality (m number) of bins with no overlapping; computing medians ($\overline{x}_k$) of $x_i'$ and medians ($\overline{y}_k$) of $y_i'$ for each bin; and interpolating the medians ($\overline{x}_k$, $\overline{y}_k$). The bins may be of equal size. In some particularly preferred embodiments, $h(x)$ is:

$$h(x) = \begin{cases} \overline{y}_1, & \text{if } x \le \overline{x}_1 \\ w\overline{y}_i + (1-w)\overline{y}_{i+1}, & \text{if } x\in(\overline{x}_i, \overline{x}_i+1], w = \frac{\overline{x}_{i+1} - x}{\overline{x}_{i+1} + -\overline{x}_i}, i = 1, \ldots, m-1, \\ \overline{y}_m, & \text{if } x > \overline{x}_m. \end{cases}$$

In one particularly preferred embodiment, m is 3.

IV. Comparative Gene Expression Analysis

The normalization factor of the invention may be used to adjust for probe array to probe array variations so that intensity values from different probe arrays may be appropriately compared. In one aspect of the invention, computer implemented methods for comparing the expression of a gene in a first sample with a second sample are also provided. One of skill in the art would appreciate that the normalization factor, methods, system and software for calculating the normalization factor of the invention are not limited to any particular method for comparison. Rather the normalization factor of the invention may be used in conjunction with other suitable statistical comparison methods not discussed in this specification.

In preferred embodiments, methods are provided to compare results from different probe arrays using the normalization factor of the invention. The methods may include the steps of providing a first plurality of intensity values ($I_i^{(1)}$), each of which reflects the expression of the gene in the first sample, where the intensity values are obtained from a first nucleic acid probe array; providing a second plurality of intensity values ($I_i^{(2)}$), each of which reflects the expression of the gene in the second sample, wherein the intensity values are obtained from a second nucleic acid probe array; calculating a p-value using one-sided Wilcoxon's signed rank test, wherein the p-value is for a null hypothesis that median($f(x)I_i^{(2)}-I_i^{(1)}$)=0 and an alternative hypothesis that median ($f(x)I_i^{(2)}-I_i^{(1)}$)>0, wherein said $f(x)$ is a normalization factor; and indicating whether the expression of gene is increased in the second sample in comparison with the first sample based upon said p-value. Each of the intensity values may be from one probe (such as a probe that is designed to target the transcript of the gene) on the nucleic acid probe arrays. One of skill in the art would appreciate that the nonparametric comparison methods of the invention are not limited to any particular normalization factors. In some embodiments, there may not be a need for any normalization factor (i.e., normalization factor=1). However, in particularly preferred embodiments, the nonparametric methods for comparative analysis employ the normalization factor of the invention.

Figure 3:
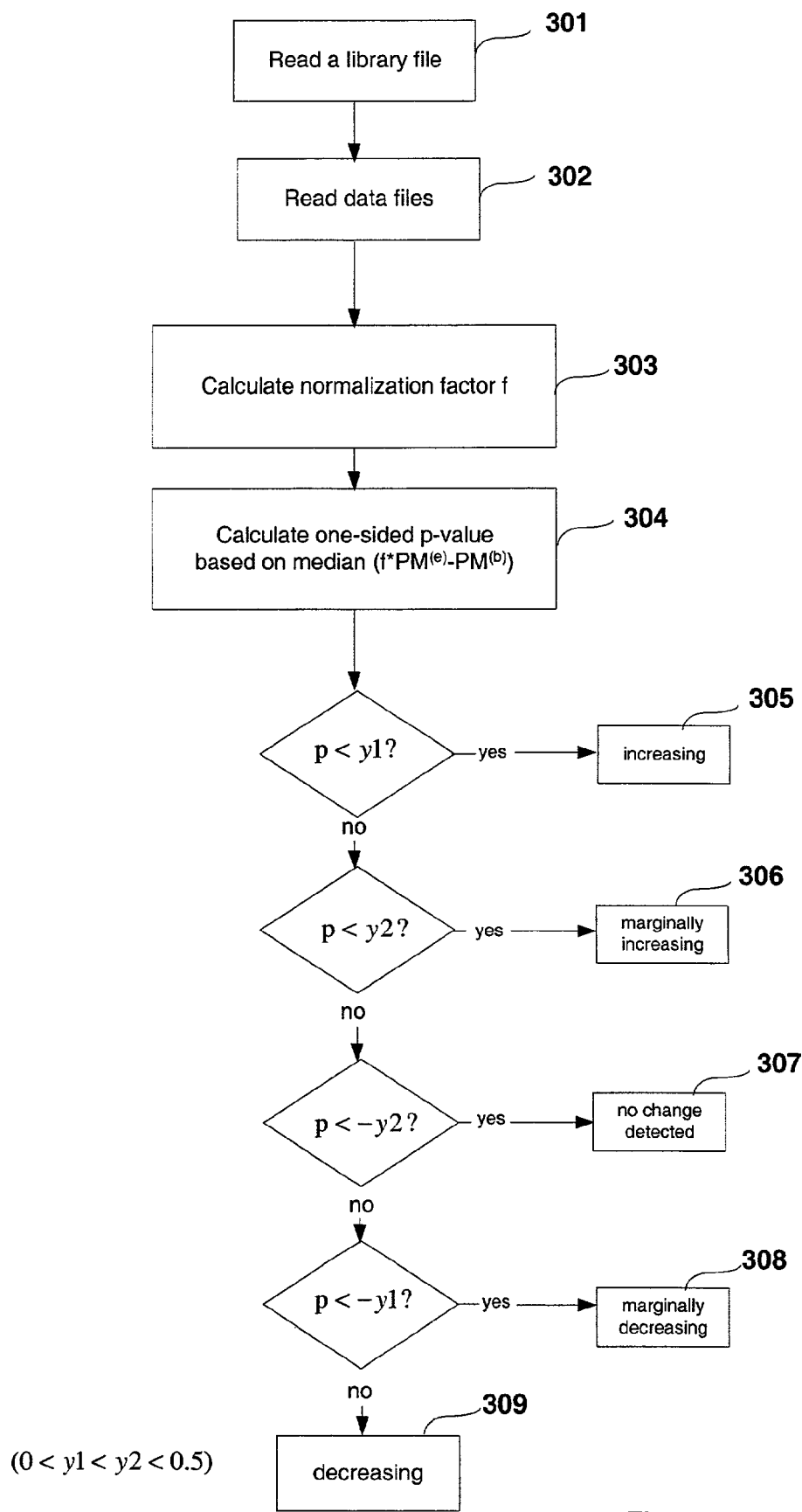
FIG. 3 shows a computerized process for comparative analysis of gene expression data from two probe arrays.

FIG. 3 shows a computerized process for comparative analysis. A library file (301) is inputted into memory. The library file contains information relating probes to their target transcripts. If the configuration of the two probe arrays to be compared (as shown in FIG. 3, the first probe array is hybridized with a base line example (b), and the second probe array is hybridized with an experimental sample (b)) are the same, the same library may be used for both probe arrays. Intensity values from two probe arrays (302) are inputted from data files. In some embodiments (as shown in FIG. 3), only intensity values for the perfect match probes may be inputted. A normalization factor is calculated (303). One-sided p-value may be calculated as described earlier (304) and appropriate calls (increasing, marginally increasing or no change detected) may be made based upon the p value.

As discussed above, the normalization factor ($f(x)$) may be calculated by obtaining the geometric mean ($x$) of $I_i^{(1)}$ and $I_i^{(2)}$; calculating the normalization factor according to: $f(x)=e^{h(x)}$, where the $h(x)$ is derived from referential intensities from the first and second probe arrays. In some embodiments, $h(x)$ is derived by relating geometric means ($x_i'$) of first referential intensities ($RI_i^{(1)}$) in the first probe array and the second referential intensities ($RI_i^{(2)}$) in said second probe array to:

$$y_i = \log\left(\frac{RI_i^{(1)}}{RI_i^{(2)}}\right).$$

In some preferred embodiments, h(x) is derived by sorting ($x_i$, $y_i$) pairs according to $x_i$ into a plurality (m number) of bins with no overlapping; computing medians ($\bar{x}_k$) of $x_i$'s and medians ($\bar{y}_k$) of $y_i$'s for each bin; and interpolating the medians ($\bar{x}_k$, $\bar{y}_k$). The bins may be of equal size. In some particularly preferred embodiments, h(x) is:

$$h(x) = \begin{cases} \bar{y}_1, \\ w\bar{y}_i + (1-w)\bar{y}_{i+1}, \\ \bar{y}_m, \end{cases}$$

$$\text{if } x \le \bar{x}_1$$
$$\text{if } x \in (\bar{x}_i, \bar{x}_i+1], \ w = \frac{\bar{x}_{i+1} - x}{\bar{x}_{i+1} + -\bar{x}_i}, i = 1, \ldots, m-1,$$
$$\text{if } x > \bar{x}_m.$$

In one particularly preferred embodiment, m is 3.

V. Example

Robust normalization factor methods were applied to six yeast test chip Latin square data sets. The first three data sets (9912072, 9913514 and 9914059) used solutions of 112 yeast genes and four bacterial spike genes BioB (1.5 pM) and BioC (5 pM), BioD (25 pM), and Crex (100 pM). The second three data sets (9912072BG, 9913514BG and 9914059BG) included human genome background.

Figure 4:
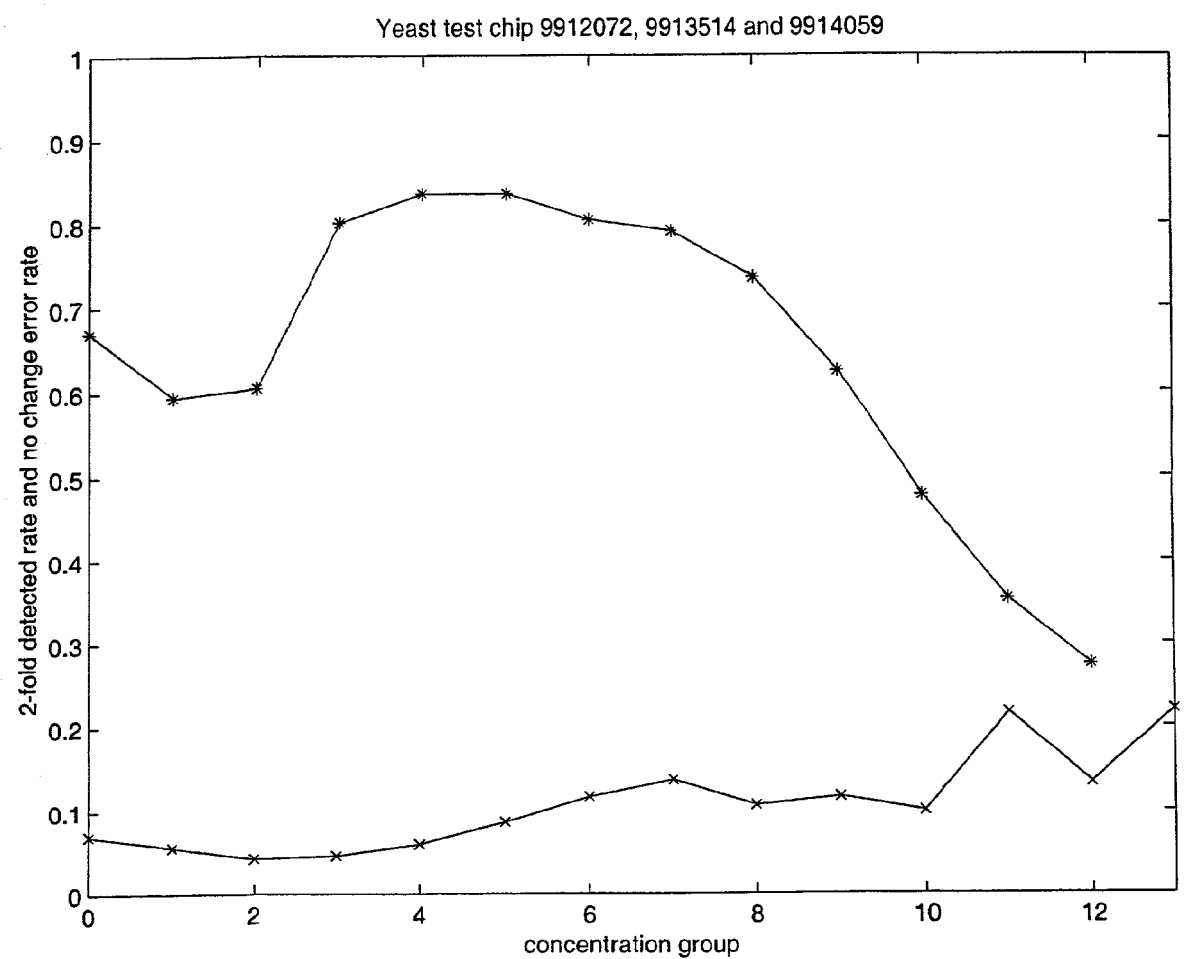
FIG. 4 shows 2 fold detected rate and no change error rate for 9912072, 9913514 and 9914059.
Figure 5:
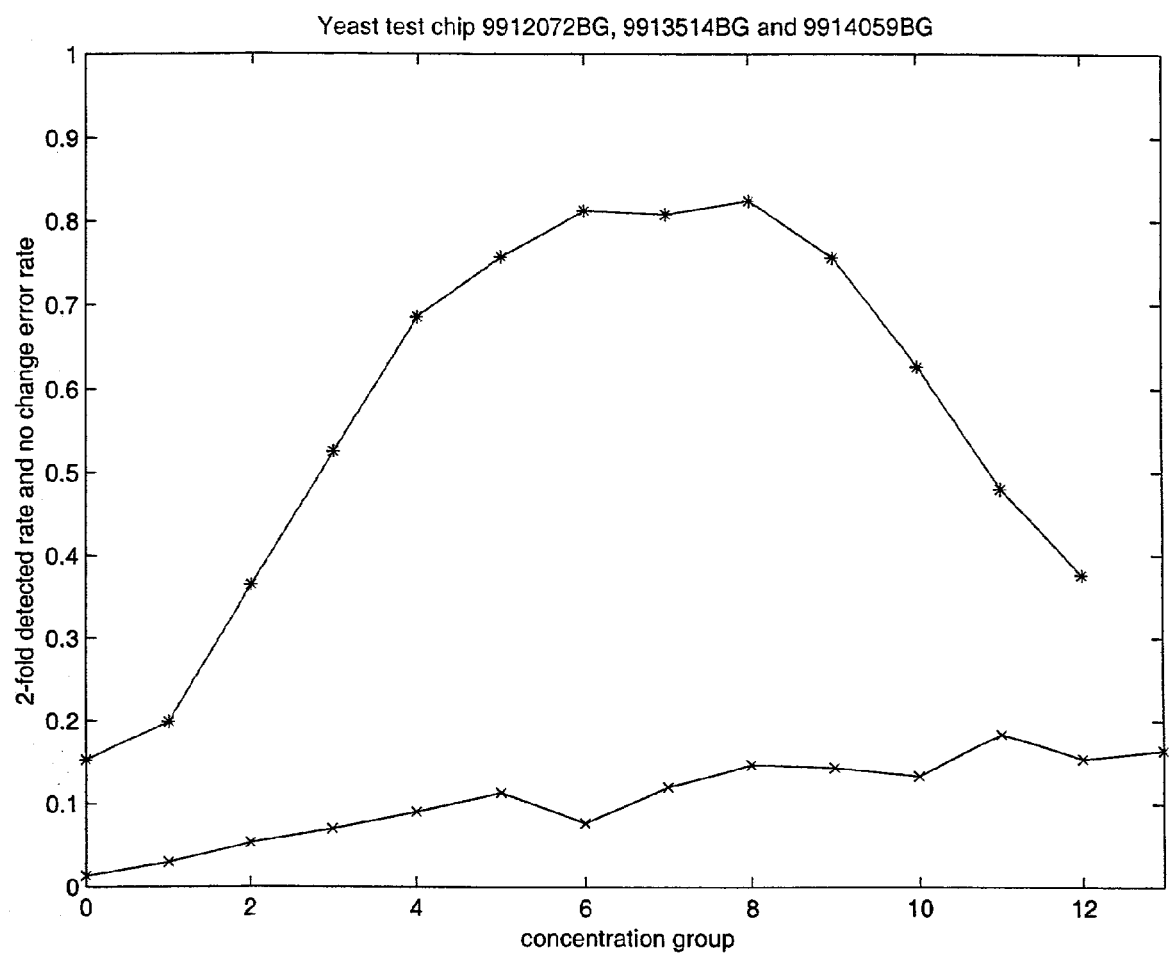
FIG. 5 shows 2 fold detected rate and no change error rate for 9912072BG, 9913514BG and 9914059BG.

The performance of the method is summarized in FIGS. 4 and 5. The upper curve shows the two-fold correctly detected comparative calls using the normalization factor and non-parametric test of the invention (0 versus 0.25 pM is also included as group 0, 0.25 pM versus 0.5 pM is considered as group 1, and 0.5 pM versus 1 pM is considered as group 2, . . . , 512 pM versus 1024 pM is considered as group 12). The lower curve shows the error rate of no change calls (0 pM versus 0 pM is considered as group 0, 0.25 pM versus 0.25 pM is considered as group 2, . . . , 1024 pM versus 1024 pM is considered as group 13.

CONCLUSION

The present invention provides methods and computer software products for analyzing gene expression profiles. It is to be understood that the above description is intended to be illustrative and not restrictive. Many variations of the invention will be apparent to those of skill in the art upon reviewing the above description. By way of example, the invention has been described primarily with reference to the use of a high density oligonucleotide array, but it will be readily recognized by those of skill in the art that other nucleic acid arrays, other methods of measuring transcript levels and gene expression monitoring at the protein level could be used. The scope of the invention should, therefore, be determined not with reference to the above description, but should instead be determined with reference to the appended claims, along with the full scope of equivalents to which such claims are entitled.

All cited references, including patent and non-patent literature, are incorporated herein by reference in their entireties for all purposes.

What is claimed is:

1. A computer implemented method for calculating a normalization factor comprising:
   providing a first intensity value ($I^{(1)}$) of a probe in a first probe array and a second intensity value ($I^{(2)}$) of said probe in a second probe array, wherein the intensity values are referential intensity values that indicate nucleic acid hybridization;
   obtaining the geometric mean (x) of said $I^{(1)}$ and said $I^{(2)}$;
   calculating said normalization factor according to:
   $f(x) = e^{h(x)}$, wherein said h(x) is derived from the referential intensity values from said first and second probe arrays; and
   using said normalization factor for gene expression analysis and outputting the result of said analysis.

2. The method of claim 1 wherein said h(x) is derived by relating geometric means ($x_i'$) of first referential intensities ($RI_i^{(1)}$) in the first probe array and second referential intensities ($RI_i^{(2)}$) in the second probe array to:

$$y_i = \log\left(\frac{RI_i^{(1)}}{RI_i^{(2)}}\right), w = \frac{\bar{x}_1 + 1 - x}{\bar{x}_1 + 1 - \bar{x}_1}, i = 1, \ldots, m-1,$$

3. The method of claim 2 wherein said relating comprising:
   sorting ($x_i$, $y_i$) pairs according to $x_i$ into a plurality (m number) of bins with no overlapping;
   computing medians ($\bar{x}_k$) of $x_i$'s and medians ($\bar{y}_k$) of $y_i$'s for each bin; and interpolating said medians ($\bar{x}_k$, $\bar{y}_k$).

4. The method of claim 3 wherein said bins are of approximately equal size.

5. The method of claim 4 wherein h(x) is:

$$h(x) = \begin{cases} \bar{y}_1, \\ w\bar{y}_1 + (1-w)\bar{y}_{1+1}, \\ \bar{y}_m, \end{cases}$$

$$\text{if } x \le \bar{x}_1$$
$$\text{if } x \in (\bar{x}_i, \bar{x}_i+1), \ w = \frac{\bar{x}_1 + 1 - x}{\bar{x}_1 + 1 - \bar{x}_i}, i = 1, \ldots, m-1,$$
$$\text{if } x > \bar{x}_m.$$

6. The method of claim 5 wherein said m is 3.

7. A system for calculating a normalization factor comprising:
   a processor; and
   a memory coupled with the processor, the memory storing a plurality of machine instructions that cause the processor to perform a plurality of logical steps when implemented by the processor, the logical steps comprising:
   providing a first intensity value ($I^{(1)}$) of a probe in a first probe array and a second intensity value ($I^{(2)}$) of said probe in a second probe array, wherein the intensity values are referential intensity values that indicate nucleic acid hybridization;
   obtaining the geometric mean (x) of said $I^{(1)}$ and said $I^{(2)}$;
   calculating said normalization factor according to:
   $f(x) \ e^{h(x)}$, wherein said h(x) is derived from the referential intensity values from said first and second probe arrays; and
   using said normalization factor for gene expression analysis and outputting the result of said analysis.

8. The system of claim 7 wherein said h(x) is derived by relating geometric means (xi') of first referential intensities ($R_i^{(1)}$) in the first probe array and second referential intensities ($R_i^{(2)}$) in the second probe array to:

$$y_i' = \log\left(\frac{RI_i^{(1)}}{RI_i^{(2)}}\right).$$

9. The system of claim 8 wherein said relating comprising:
 sorting ($x_i$, $y_i$) pairs according to $x_i$ into a plurality (m number) of bins with no overlapping;
 computing medians ($\bar{x}_k$) of $x_i$'s and medians ($\bar{y}_k$) of $y_i$'s for each bin; and
 interpolating said medians ($\bar{x}_k$, $\bar{y}_k$).

10. The system of claim 9 wherein said bins are of approximately equal size.

11. The system of claim 10 wherein said h(x) is:

$$h(x) = \begin{cases} \bar{y}_1, \\ w\bar{y}_i + (1-w)\bar{y}_{i+1}, \\ \bar{y}_m, \end{cases}$$

$$\text{if } x \leq \bar{x}_1$$
$$\text{if } x \in (\bar{x}_i, \bar{x}_i+1], \ w = \frac{\bar{x}_{i+1} - x}{\bar{x}_{i+1} + -\bar{x}_i}, i = 1, \ldots, m-1,$$
$$\text{if } x > \bar{x}_m.$$

12. The system of claim 11 wherein said m is 3.

13. A computer software product for calculating a normalization factor comprising:
 computer program code for providing a first intensity value ($I^{(1)}$) of a probe in a first probe array and a second intensity value ($I^{(2)}$) of said probe in a second probe array, wherein the intensity values are referential intensity values that indicate nucleic acid hybridization;
 computer program code for obtaining the geometric mean (x) of said $I^{(1)}$ and said $I^{(2)}$;
 computer program code for calculating said normalization factor according to:
 $f(x)=e^{h(x)}$, wherein said h(x) is derived from the referential intensity values from said first and second probe arrays; and
 computer program code for using said normalization factor for gene expression analysis and outputting the result of said analysis; and
 a computer readable medium for storing said codes.

14. The computer software product of claim 13 wherein said h(x) is derived by relating geometric means ($x_i'$) of first referential intensities ($RI_i^{(1)}$) in the first probe array and second referential intensities ($RI_i^{(2)}$) in the second probe array to:

$$y_i = \log\left(\frac{RI_i^{(1)}}{RI_i^{(2)}}\right), w = \frac{\bar{x}_1 + 1 - x}{\bar{x}_1 + 1 - \bar{x}_1}, i = 1, \ldots, m-1,$$

15. The computer software product of claim 14 wherein said code for relating comprising:
 computer program code for sorting ($x_i$, $y_i$) pairs according to x1 into a plurality (m number) of bins with no overlapping;
 computer program code for computing medians ($\bar{x}_k$) of $x_i$'s and medians ($\bar{y}_k$) of $y_i$'s for each bin; and
 computer program code for interpolating said medians ($\bar{x}_k$, $\bar{y}_k$).

16. The computer software product of claim 15 wherein said bins are of approximately equal size.

17. The computer software product of claim 16 wherein said h(x) is:

$$h(x) = \begin{cases} \bar{y}_1, \\ w\bar{y}_1 + (1-w)\bar{y}_{1+1}, \\ \bar{y}_m, \end{cases}$$

$$\text{if } x \leq \bar{x}_1$$
$$\text{if } x \in (\bar{x}_i, \bar{x}_i+1), \ w = \frac{\bar{x}_1 + 1 - x}{\bar{x}_1 + 1 - \bar{x}_i}, i = 1, \ldots, m-1,$$
$$\text{if } x > \bar{x}_m.$$

18. The computer software product of claim 17 wherein said m is 3.

* * * * *